(12) United States Patent
Boukhny

(10) Patent No.: US 6,402,769 B1
(45) Date of Patent: Jun. 11, 2002

(54) TORSIONAL ULTRASOUND HANDPIECE

(75) Inventor: Mikhail Boukhny, Laguna Beach, CA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/489,093

(22) Filed: Jan. 21, 2000

Related U.S. Application Data

(63) Continuation-in-part of application No. 09/106,223, filed on Jun. 29, 1998, now Pat. No. 6,077,285.

(51) Int. Cl.⁷ .................................................. A61F 9/00
(52) U.S. Cl. ......................................... 606/169; 604/22
(58) Field of Search ................................ 606/166, 169, 606/167, 170, 171, 180; 604/22

(56) References Cited

U.S. PATENT DOCUMENTS

| | | | |
|---|---|---|---|
| 3,526,219 A | * | 9/1970 | Balamuth ....................... 128/2 |
| 3,589,363 A | | 6/1971 | Banko et al. |
| 4,223,676 A | | 9/1980 | Wuchinich et al. |
| 4,493,694 A | | 1/1985 | Wuchinich |
| 4,504,264 A | | 3/1985 | Kelman |
| 4,515,583 A | | 5/1985 | Sorich |
| 4,589,415 A | | 5/1986 | Haaga |
| 4,609,368 A | | 9/1986 | Dotson, Jr. |
| 4,869,715 A | | 9/1989 | Sherburne |
| 4,922,902 A | | 5/1990 | Wuchinich et al. |
| 5,222,959 A | | 6/1993 | Anis |
| 5,431,664 A | | 7/1995 | Ureche et al. |
| 5,676,649 A | | 10/1997 | Boukhny et al. |
| 5,722,945 A | | 3/1998 | Anis et al. |

FOREIGN PATENT DOCUMENTS

WO          WO 00/00298 A          1/2000

OTHER PUBLICATIONS

Lin Shuyu, "Sandwiched Piezoelectric Ultrasonic Transducers of Longitudinal–Torsional Compound Vibrational Modes", IEEE Transactions on Ultrasonics, Ferrelectrics, and Frequency Control, vol. 44, No. 6, Nov. 1997, pp. 1189–1197.

* cited by examiner

Primary Examiner—Henry J. Recla
Assistant Examiner—Vy Q. Bui
(74) Attorney, Agent, or Firm—Jeffrey S. Schira

(57) ABSTRACT

A handpiece having at least one set of piezoelectric elements. The piezoelectric elements are constructed of segments that produce both longitudinal and torsional motion. An appropriate ultrasound driver drives the set of elements at the respective resonant frequencies to product longitudinal vibration and torsional oscillation.

3 Claims, 5 Drawing Sheets

TORSIONAL ULTRASOUND HANDPIECE

This application is a continuation-in-part application of U.S. patent application Ser. No. 09/106,223, filed Jun. 29, 1998 now U.S. Pat. No. 6,077,285.

This invention relates to ultrasonic devices and more particularly to an ophthalmic phacoemulsification handpiece.

BACKGROUND OF THE INVENTION

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, scera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

There have been prior attempts to combine ultrasonic longitudinal motion of the cutting tip with rotational or oscillating motion of the tip, see U.S. Pat. Nos. 5,222,959 (Anis), U.S. Pat. No. 5,722,945 (Anis, et al.) and U.S. Pat. No. 4,504,264 (Kelman), the entire contents of which are incorporated herein by reference. These prior attempts have used electric motors to provide the rotation of the tip which require O-ring or other seals that can fail in addition to the added complexity and possible failure of the motors.

Accordingly, a need continues to exist for a reliable ultrasonic handpiece that will vibrate both longitudinally and torsionally.

BRIEF SUMMARY OF THE INVENTION

The present invention improves upon prior art ultrasonic devices by providing a handpiece having at least one set of piezoelectric elements. The piezoelectric elements are constructed of segments that produce both longitudinal and torsional motion. An appropriate ultrasound driver drives the set of elements at the respective resonant frequencies to produce longitudinal vibration and torsional oscillation.

It is accordingly an object of the present invention to provide an ultrasound handpiece having both longitudinal and torsional motion.

It is a further object of the present invention to provide an ultrasound handpiece having a pair of piezoelectric elements polarized to produce longitudinal motion and a pair of piezoelectric elements polarized to produce torsional motion.

Other objects, features and advantages of the present invention will become apparent with reference to the drawings, and the following description of the drawings and claims.

DETAILED DESCRIPTION OF THE INVENTION

Figure 1:
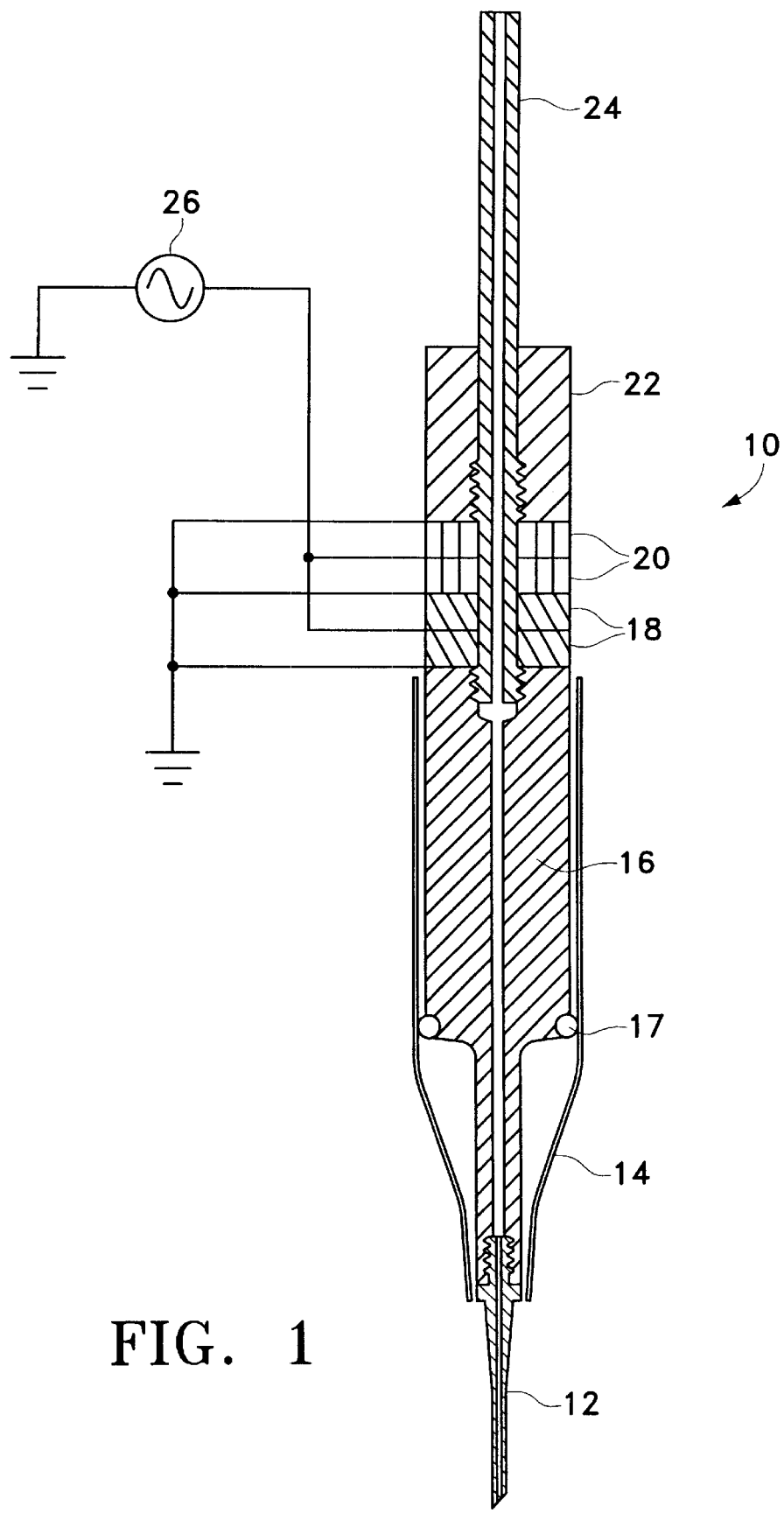
FIG. 1 is a cross-sectional view of one embodiment of an ultrasound handpiece of the present invention.

As best seen in FIG. 1, one embodiment of handpiece 10 suitable for use with the present invention generally has cutting tip 12, handpiece shell 14, ultrasound horn 16, torsional ultrasound crystals 18 and longitudinal ultrasound crystals 20. Horn 16 is held within shell 14 by isolator 17. Crystals 18 and 20 are held within shell 14 and in contact with horn 16 by back cylinder 22 and bolt 24. Crystals 18 and 20 vibrate ultrasonically in response to a signal generated by ultrasound generator 26. Crystals 18 are polarized to produce torsional motion. Crystals 20 are polarized to produce longitudinal motion.

Figure 6:
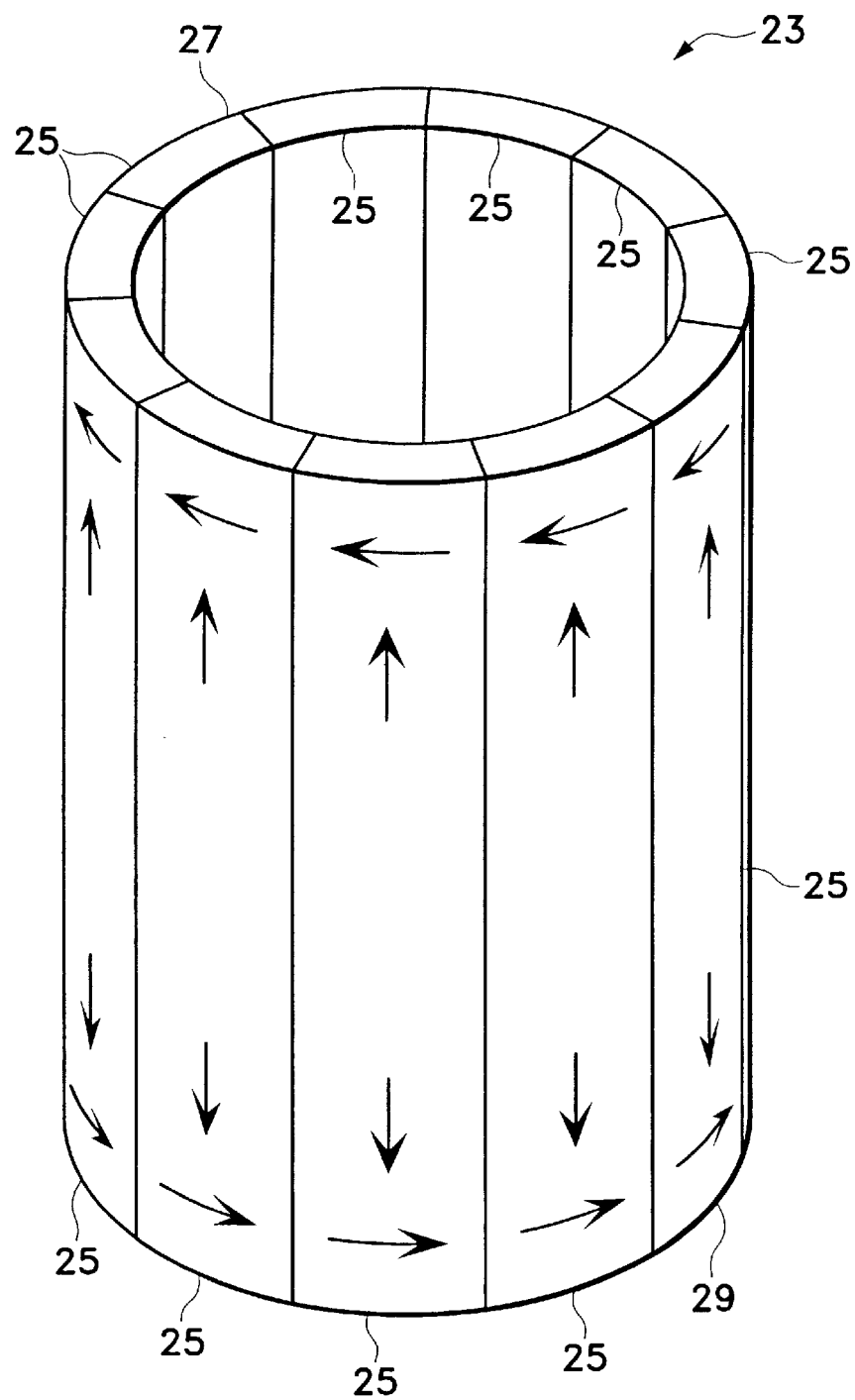
FIG. 6 is a perspective view of an ultrasonic piezoelectric crystal that may be used with the present invention.

Alternatively, as illustrated in FIG. 6, crystal 23 may be used to produce both longitudinal and torsional motion. Crystal 23 is generally ring shaped, resembling a hollow cylinder, and is constructed from a plurality of crystal segments 25. Upper portions 27 of segments 25 may be polarized to produce clockwise motion while lower portions 29 of segments 25 may be polarized to produce counterclockwise motion or vice versa. When segments 25 are assembled into crystal 23, the polarization of segments 25 cause crystal 23 to twist when excited. In addition, the twisting motion of crystal 23 will produce longitudinal motion, but such longitudinal motion will resonate at a different resonant frequency than the torsional motion. For example, torsional movement in crystal 23 can occur at approximately between 18 kilohertz (Khz) and 25 Khz while longitudinal motion in crystal 23 can occur at approximately between 33 Khz and 43 Khz, with approximately 21 Khz and approximately 38 Khz, respectively, being preferred. This difference is because the forces on crystal 23 resisting such vibrations are different in the torsional direction than in the longitudinal direction. One skilled in the art will recognize that different frequencies may be used depending upon the construction of crystal 23. By subjecting crystal 23 to two drive signals, one at the torsional resonant frequency and one at the longitudinal resonant frequency, both torsional and longitudinal motion can be produced in crystal 23. Handpiece 10 may can any suitable number of pairs of crystals 23, for example a single pair or two pairs.

Figure 2:
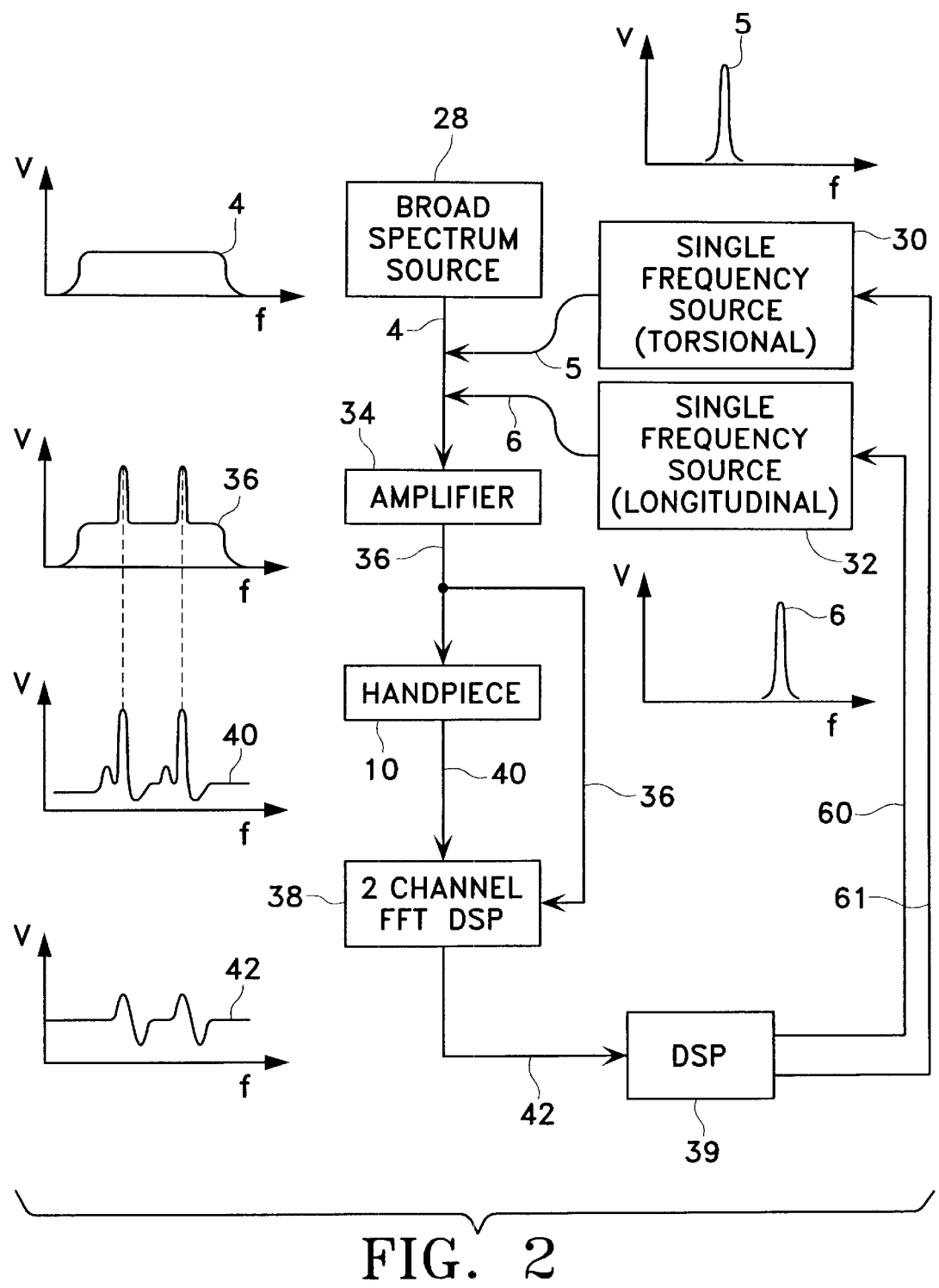
FIG. 2 a block diagram of a first driving circuit that may be used with the present invention.
Figure 3:
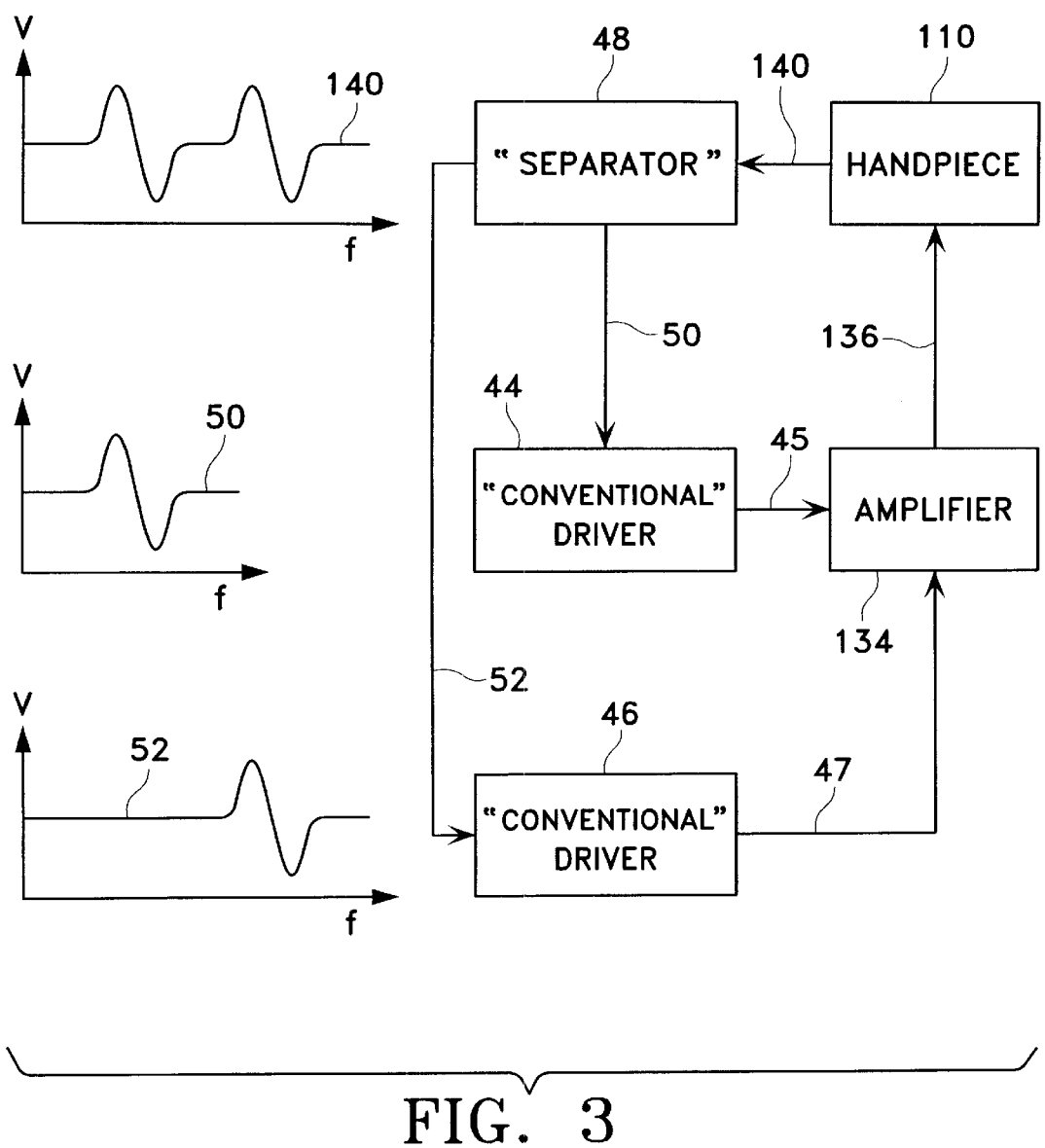
FIG. 3 is a block diagram of a second driving circuit that may be used with the present invention.

As seen in FIG. 2, ultrasound generator 26 employs a broad-spectrum source to generate at least a component of the signal that drives an ultrasonic handpiece ("the drive signal"). The broad-spectrum source may be programmable and thus easily adjustable by varying certain input information fed to the source. However, a fixed-spectrum source may also be used without difficulty. A fast fourier transform ("FFT") digital signal processor ("DSP") may be used to analyze the response of handpiece 10 to the broad-spectrum component of the drive signal. In real-time applications, the output of the FFT DSP is used to generate control parameters embodied within an appropriate feedback signal, which is fed to the circuitry generating the drive signal in order to alter aspects of the drive signal. As seen in FIG. 3, ultrasound generator 26 may also use a conventional signal processor to analyze the response of handpiece 10 to the drive signal. The term "drive signal" as used here encompasses at least a signal useful solely for powering an ultrasonic handpiece, a signal useful solely for tuning or calibrating a handpiece, and a combination of such a power signal and such a tuning or calibration signal.

As shown in FIG. 2, broad spectrum signal source 28 generates drive signal 4 which is combined with drive signals 5 and 6 from torsional single frequency source 30 and longitudinal single frequency source 32, respectively, in amplifier 34. Amplifier 34 delivers drive signal 36 to handpiece 10 and to FFT DSP 38. FFT DSP 38 also receives feedback signal 40 from handpiece 10. FFT DSP 38 processes drive signal 36 and feedback signal 40 in the manner more fully disclosed in commonly owned U.S. patent application Ser. No. 08/769,257 (corresponding to PCT Patent Application No. PCT/US97/15952), the entire contents of which being incorporated herein by reference, to determine the operating characteristics of handpiece 10. FFT DSP 38 determines the electrical response of handpiece 10 on broad spectrum signal 4 and provides signal 42 to DSP 39 which generates adjusting signals 60 and 61 to adjust the frequencies and/or output voltage of sources 32 and 30, respectively so as to adjust drive signals 5 and 6.

As shown in FIG. 3, two conventional drive signal sources, such as those described in U.S. Pat. No. 5,431,664, the entire contents of which is incorporated herein by reference, or U.S. patent application Ser. No. 08/769,257 (corresponding to PCT Patent Application No. PCT/US97/15952), may be used. For example, source 44 may generate drive signal 45 for torsional crystals 18 and source 46 may generate driving signal 47 for longitudinal crystals 20. Drive signals 45 and 47 are combined in amplifier 134 and drive signal 136 delivered to handpiece 110. Handpiece feedback signal 140 is filtered through separator 48 to provide adjusting signals 50 and 52 to sources 44 and 46. Separator 48 may be any number of commercially available analog or digital devices such low pass or high pass filters or heterodyne receiver.

Figure 4:
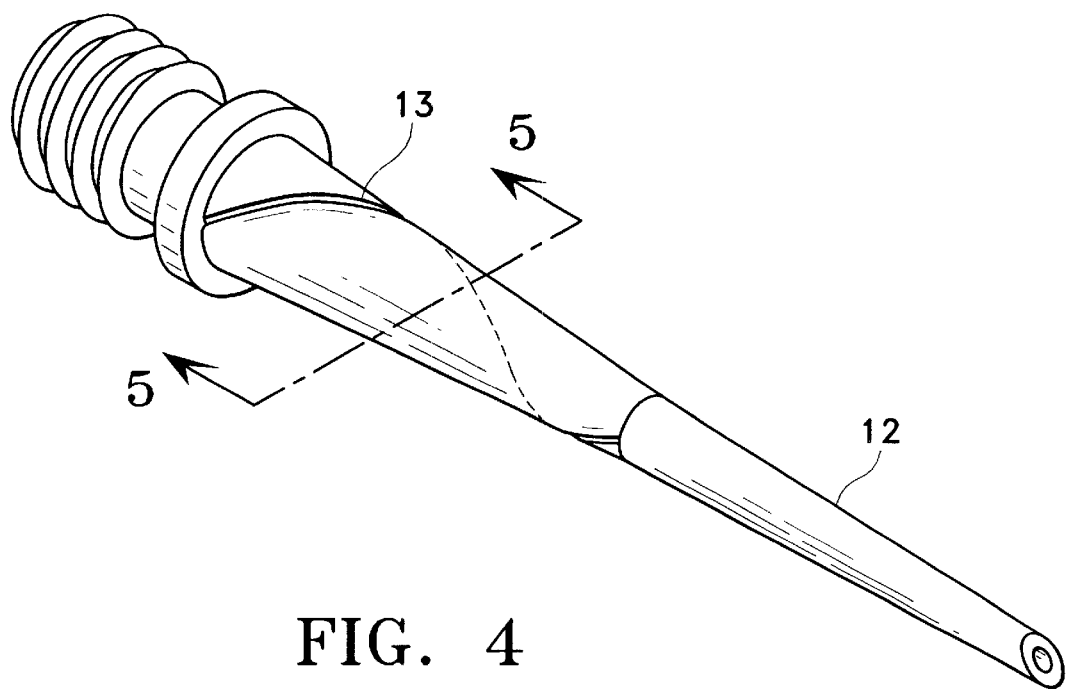
FIG. 4 is a perspective view of a phacoemulsification tip that may be used with the present invention.
Figure 5:
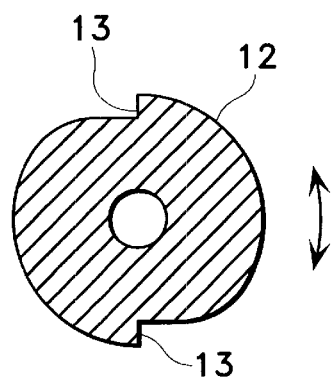
FIG. 5 is a cross-sectional view of the phacoemulsification tip illustrated in FIG. 4 taken at line 5—5 in FIG. 4.

The torsional motion of horn 16 may cause cutting tip 12 to loosen. In order to reduce the chances of cutting tip 12 becoming loose, tip 12 may be asymmetrically shaped, as seen in FIGS. 4 and 5. This asymmetric shape can be accomplished by cutting spiral thread 13 in tip 12 to increase the hydrodynamic forces on tip 12 in the manner more fully described in U.S. Pat. No. 5,676,649, the entire contents of which being incorporated herein by reference.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An ultrasound surgical handpiece, comprising:

a) a handpiece shell;

b) an ultrasound horn held within the shell;

c) at least one pair of ultrasound crystals polarized to produce longitudinal motion when subjected to a first drive frequency and torsional motion when subjected to a second drive frequency, the crystals held in contact with the ultrasound horn; and d) a cutting tip mounted on the horn opposite the crystals;

wherein one of the frequencies is approximately between 18 kilohertz and 25 kilohertz and the other frequency is approximately between 33 kilohertz and 43 kilohertz.

2. The handpiece of claim 1, wherein the cutting tip is asymmetrically shaped.

3. The handpiece of claim 1, wherein the crystals are constructed of crystal segments.

* * * * *